United States Patent
Conti et al.

(10) Patent No.: US 9,222,836 B2
(45) Date of Patent: Dec. 29, 2015

(54) HAIR COLORANT SYSTEM AND METHOD

(71) Applicants: Aaron James Conti, Palatine, IL (US); Donald James Conti, Palatine, IL (US); Jon F. Maple, Orlando, FL (US); Patrick J. McIvor, Jr., Nazareth, PA (US); Leonard G. Case, Seattle, WA (US)

(72) Inventors: Aaron James Conti, Palatine, IL (US); Donald James Conti, Palatine, IL (US); Jon F. Maple, Orlando, FL (US); Patrick J. McIvor, Jr., Nazareth, PA (US); Leonard G. Case, Seattle, WA (US)

( * ) Notice: Subject to any disclaimer, the term of this patent is extended or adjusted under 35 U.S.C. 154(b) by 0 days.

(21) Appl. No.: 13/666,117

(22) Filed: Nov. 1, 2012

(65) Prior Publication Data
US 2014/0118521 A1    May 1, 2014

(51) Int. Cl.
*G01J 3/52* (2006.01)
*G01J 3/02* (2006.01)
*G01J 3/46* (2006.01)
*H04N 7/18* (2006.01)

(52) U.S. Cl.
CPC .............. *G01J 3/524* (2013.01); *G01J 3/0202* (2013.01); *G01J 3/0256* (2013.01); *G01J 3/0264* (2013.01); *G01J 3/0267* (2013.01); *G01J 3/462* (2013.01); *G01J 3/52* (2013.01); *G01J 2003/466* (2013.01); *H04N 7/18* (2013.01)

(58) Field of Classification Search
CPC .............. H04N 2005/2726; G01J 3/46; G01J 2003/466; G01J 3/0202; G01J 3/0267
USPC ................................................ 382/100, 162
See application file for complete search history.

(56) References Cited

U.S. PATENT DOCUMENTS

| | | | |
|---|---|---|---|
| 6,627,372 B1* | 9/2003 | Steinhauer et al. ........ | 430/137.1 |
| 7,057,641 B2* | 6/2006 | Bodnar et al. ............... | 348/188 |
| 7,110,117 B2 | 9/2006 | Grossinger et al. | |
| 7,463,556 B2 | 12/2008 | Hocherman | |
| D657,703 S | 4/2012 | Stegmann et al. | |
| D683,641 S | 6/2013 | Stegmann et al. | |
| D689,386 S | 9/2013 | Stegmann et al. | |
| 2001/0052904 A1* | 12/2001 | Sano et al. ..................... | 345/589 |
| 2004/0179101 A1 | 9/2004 | Bodnar et al. | |
| 2005/0165705 A1 | 7/2005 | Lauper et al. | |
| 2005/0256733 A1 | 11/2005 | Nagai et al. | |
| 2006/0195300 A1 | 8/2006 | Grossinger et al. | |

(Continued)

FOREIGN PATENT DOCUMENTS

| | | |
|---|---|---|
| WO | 2009152033 A1 | 12/2009 |
| WO | 2010100231 A1 | 9/2010 |
| WO | 2012127429 A2 | 9/2012 |

OTHER PUBLICATIONS

International Search Report and Written Opinion for International Application No. PCT/US2013/047247 mailed Nov. 22, 2013.
Rousset et al., Frequential and color analysis for hair mask segmentation. 15th IEEE International Conference on Image Processing [online], 2008 [Retrieved on Oct. 31, 2013] pp. 2276-2279.

(Continued)

*Primary Examiner* — Yubin Hung
(74) *Attorney, Agent, or Firm* — Jeffrey T. Placker; Holland & Knight LLP (57) ABSTRACT

A system and method for improving the outcome and consistency of hair coloring is provided. In an example method, an image of hair having a sample color may be received. A color space characteristic associated with the hair sample may be determined. An indication of a target color may be received. A colorant formulation may be identified for changing the hair from the sample color to the target color.

5 Claims, 8 Drawing Sheets (56) References Cited

U.S. PATENT DOCUMENTS

| | | |
|---|---|---|
| 2007/0143082 A1* | 6/2007 | Degnan ............................. 703/1 |
| 2007/0184415 A1 | 8/2007 | Sasaki |
| 2008/0013077 A1 | 1/2008 | Orelli et al. |
| 2008/0068604 A1 | 3/2008 | Grossinger et al. |
| 2008/0260243 A1* | 10/2008 | Occelli ......................... 382/165 |
| 2009/0309962 A1* | 12/2009 | Higuchi .......................... 348/77 |
| 2010/0088036 A1* | 4/2010 | Goddard-Clark et al. ...... 702/19 |
| 2010/0299106 A1 | 11/2010 | Audoly et al. |
| 2011/0055054 A1* | 3/2011 | Glasson ....................... 705/27.2 |
| 2011/0313885 A1 | 12/2011 | Mourad et al. |
| 2012/0075331 A1 | 3/2012 | Mallick et al. |

OTHER PUBLICATIONS

Xiao et al., Object-Based Image Recoloring Using Alpha Matte and Color Histogram Specification. Interactive Technology and Sociotechnical systems [online], 2006 [Retrieved on Oct. 31, 2013], Lecture Notes in Computer Science, vol. 4270, pp. 194-203. Abstract only.

International Preliminary Report on Patentability for International Application No. PCT/US2013/047247 mailed May 5, 2015, pp. 1-9.

* cited by examiner

HAIR COLORANT SYSTEM AND METHOD

TECHNICAL FIELD

The present disclosure generally relates to hair colorant formulations, and more particularly relates to systems and methods for determining hair colorant formulations for achieving a desired color change.

BACKGROUND OF THE DISCLOSURE

Hair coloring treatments are a very common hair styling procedure. Hair coloring treatments generally utilize various combinations of chemicals to alter the color of a person's hair. For example, peroxides may be utilized to lighten the color of a person's hair. Various different chemicals may be utilized to darken and/or change hues, undertones, and the like of a person's hair. Often manufacturers of hair coloring systems may provide various chemical components that may be used to achieve different levels of change in hair color. Properly determining a person's starting hair color, before the hair coloring treatment, is an aspect of obtaining a desired final hair color. Properly determining the starting hair color can be a challenging task, that may be influenced by many factors, such as the skill and experience of the person making the determination, the quality of lighting, the color of the person's hair, the person's skin tone, as well as various additional factors. All of these factors can make achieving a desired final hair color a challenge.

SUMMARY OF THE DISCLOSURE

According to an embodiment, a computer-implemented method may include receiving an image of hair having a sample color. The method may also include determining a color space characteristic associated with the hair sample. The method may also include receiving an indication of a target color. The method may further include identifying a colorant formulation for changing the hair from the sample color to the target color.

One or more of the following features may be included. The image may include one or more calibration features. The one or more calibration features may include control color patches. The color space may include a CIELAB color space, and the characteristic may include at least a lightness characteristic. Receiving the indication of the target color may include receiving a selection from a library of colors associated with a colorant line. Receiving the indication of the target color may include receiving an image including the target color.

The method may also include calculating a color space characteristic difference between the sample color and the target color. Identifying the colorant formulation may be based on, at least in part, the color space characteristic difference between the sample color and the target color.

The method may also include receiving hair health data associated with the hair. The hair health data may include one or more of hair thickness data, hair breaking strength data, and hair elasticity data. Identifying the colorant formulation may be based on, at least in part, the hair health data. The method may also include transmitting the colorant formulation to a dispensing or mixing apparatus.

According to another embodiment, a computer program product resides on a non-transitory, computer readable medium that has a plurality of instructions stored on it. When executed by a processor, the instructions may cause the processor to perform operations including receiving an image of hair having a sample color. The instructions may also cause the processor to determine a color space characteristic associated with the hair sample. The instructions may also cause the processor to receive an indication of a target color. The instructions may further cause the processor to identify a colorant formulation for changing the hair from the sample color to the target color.

One or more of the following features may be included. The image may include one or more calibration features. The one or more calibration features may include control color patches. The color space may include a CIELAB color space, and the characteristic may include at least a lightness characteristic.

The instructions for receiving the indication of the target color may include instructions for receiving a selection from a library of colors associated with a colorant line. The instructions for receiving the indication of the target color may include instructions for receiving an image including the target color. Instructions may also be included for calculating a color space characteristic difference between the sample color and the target color. Identifying the colorant formulation may be based on, at least in part, the color space characteristic difference between the sample color and the target color.

Instructions may also be included for receiving hair health data associated with the hair. The hair health data may include one or more of hair thickness data, hair breaking strength data, and hair elasticity data. The instructions for identifying the colorant formulation may be based on, at least in part, the hair health data. Instructions may also be included for transmitting the colorant formulation to a dispensing and mixing apparatus.

According to yet another embodiment an apparatus may include a body portion having a slot extending through a portion thereof. The body portion may also include a guide feature proximate the slot. The guide feature may be configured to assist directing hair into the slot. The guide feature may include one or more of a fixed projection and a removable projection. The apparatus may also include an imaging window disposed at least partially within the body portion and adjacent a proximal region of the slot. The imaging window may include a calibration feature disposed on an imaging plane of the imaging window. An illumination unit may be configured to illuminate a region proximate the imaging plane of the imaging window. An imaging unit may include an imaging element arranged to acquire an image in a region adjacent the imaging plane of the imaging window.

One or more of the following features may be included. The calibration feature may include one or more color patches. The calibration feature may include a feature having a known dimension. The body portion may be configured to be coupled with a mobile computing device. The imaging unit may include one or more processors configured to output an image acquired by the imaging unit to a computing device.

The details of one or more implementations are set forth in the accompanying drawings and the description below. Other features and advantages will become apparent from the description, the drawings, and the claims.

DETAILED DESCRIPTION OF EXAMPLE EMBODIMENTS

Figure 1:
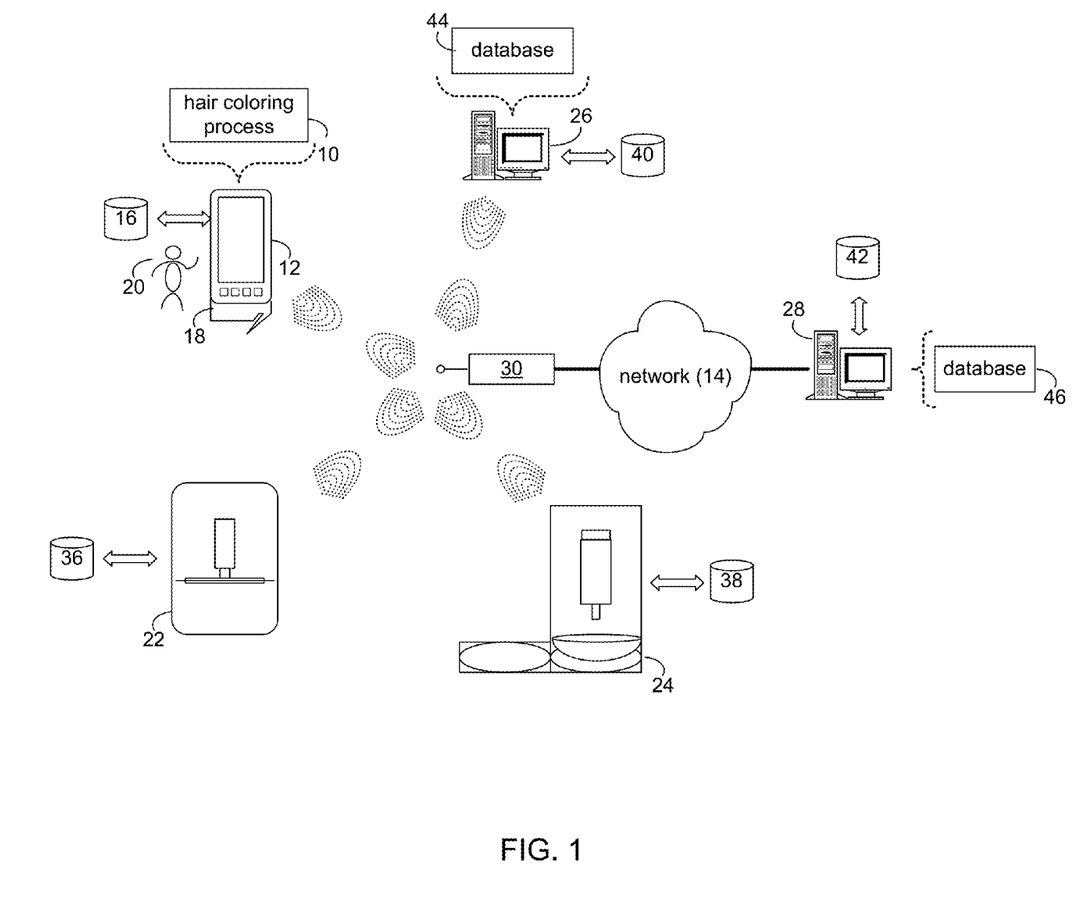
FIG. 1 is a diagrammatic view of a distributed computing network including a computing device that executes a hair coloring process according to an embodiment of the present disclosure.

Referring to FIG. 1, there is shown hair coloring process 10 that may reside on and may be executed by computing device 12. Examples of computing device 12 may include, but are not limited to: a mobile computing device (e.g., a smartphone, a tablet computing device, or the like), a personal computer, a notebook computer, or the like.

As will be described in greater detail below, according to an example embodiment hair coloring process 10 may generally receive an image of hair having a sample color. Hair coloring process 10 may also determine a CIELAB color space characteristic associated with the hair sample. Hair coloring process 10 may also receive an indication of a target color. Hair coloring process 10 may further identify a colorant formulation for changing the hair from the sample color to the target color.

The instruction sets and subroutines of hair coloring process 10, which may include one or more software modules, and which may be stored on storage device 16 coupled to computing device 12, may be executed by one or more processors (not shown) and one or more memory modules (not shown) incorporated into computing device 12. Storage device 16 may include but is not limited to: a hard disk drive; a solid state drive, a tape drive; an optical drive; a RAID array; a random access memory (RAM); and a read-only memory (ROM). Computing device 12 may execute an appropriate operating system, for example, Mac OS, iOS, Android OS, Windows, or other suitable operating system. (Mac OS is a trademark of Apple Inc. in the United States, other countries, or both; iOS is a trademark of Cisco Systems, Inc.; Android is a trademark of Google Inc. in the United States, other countries, or both; Windows is a trademark of Microsoft Corporation in the United Sates, other countries, or both.)

Hair coloring process 10 may interface and/or interact with one or more additional devices. For example, hair coloring process 10 may interact with hair color measurement device 18. As will be described in greater detail below, hair color measurement device 18 may generally be utilized by a user (e.g. user 20) to determine one or more color characteristics of a sample of hair. Hair coloring process 10 may also interact with hair health analyzer 22. As will be described in greater detail below, hair health analyzer 22 may generally be utilized by a user (e.g., user 20) to determine one or more hair health characteristics associated with the sample of hair. Further, hair coloring process 10 may interact with dispensing and mixing apparatus 24. As will be described in greater detail below, dispensing and mixing apparatus 24 may generally be utilized by a user (e.g., user 20) to dispense and/or mix colorant components to produce a hair colorant formulation. Additionally, hair coloring process 10 may interact with one or more additional computing devices (e.g., personal computer 26, server computer 28, a notebook computer, a gaming console, or other computing device).

Computing device 12 may be directly and/or indirectly coupled to one or more of hair color measurement device 18, hair health analyzer 22, dispensing and mixing apparatus 24, personal computer 26 and server computer 28. For example, as shown computing device 12 may be directly coupled to hair color measurement device 18 (e.g., via a universal serial bus ("USB") interface, or other suitable interface). Further, computing device 12 may be wirelessly coupled to hair health analyze 22, dispensing and mixing apparatus 24 and personal computer 26. For example, computing device 12 may be directly coupled to one or more of hair health analyzer 22, dispensing and mixing apparatus 24 and/or personal computer 26 via a suitable wireless protocol (e.g., Bluetooth, Wi-Fi, etc.). In some embodiments, computing device 12 may be wirelessly coupled with one or more of hair health analyzer 22, dispensing and mixing apparatus 24 and/or personal computer 26 via a wireless access point (e.g., access point 30, which may include an IEEE 802.11a, 802.11b, 802.11g, 802.11n Wi-Fi device, Bluetooth device, and/or another device that is capable of establishing a wireless communication channel between computing device and one or more other devices). Additionally, computing device 12 may be coupled to server computer 28 via network 14, examples of which may include, but are not limited to, a local area network, a wide area network, the Internet, or other network. Further, while not shown, computing device 12 may be coupled to one or more of hair health analyzer 22, dispensing and mixing apparatus 24, and/or personal computer 26 via one or more networks (e.g., which may include a personal area network, a local area network, a wide area network, the Internet, or other network or a combination of various types of networks).

As is known in the art, all of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. As is known in the art, Bluetooth is a telecommunications industry specification that allows devices, e.g., mobile phones, computers, and personal digital assistants, to be interconnected using a short-range wireless connection.

While computing device 12 is shown wirelessly coupled to one or more of hair health analyzer 22, dispensing and mixing apparatus 24, personal computer 26 and network 14 (and thereby to server computer 28), such depiction is intended only for the purpose of illustrations. Computing device 12 may be coupled to one or more of hair health analyzer 22, dispensing and mixing apparatus 24, personal computer 26, and network 14 via a wired connection (e.g. using any suitable connection type and/or communication protocol, such as an Ethernet connection, USB connection, etc.). Further, one or more of hair health analyzer 22, dispensing and mixing apparatus 24, personal computer 26 and server computer 28 may be directly, or indirectly coupled to one another.

In some embodiments, hair coloring process 10 may include a hybrid application, in which some of the functionality of hair coloring process 10 may be implemented on computing device 12, and in which some of the functionality of hair coloring process 10 may be implemented on another computing device (e.g., hair color measurement device 18, hair health analyzer 22, dispensing and mixing apparatus 24, personal computer 26, and server computer 28). In such an embodiment, the instruction sets and subroutines of hair coloring process (and/or portions, modules, and functionalities thereof) may be stored on storage devices 16, 36, 38, 40, 42 (respectively) coupled to hair color device 18, hair health analyzer 22, dispensing and mixing apparatus 24, personal computer 26 and server computer 28 (respectively), and may be executed by one or more processors (not shown) and one or more memory modules (not shown) incorporated into hair color measurement device 18, hair health analyzer 22, dispensing and mixing apparatus 24, personal computer 26, and server computer 28. Storage devices 16, 36, 38, 40, 42 may include but are not limited to: hard disk drives; solid state drives, tape drives; optical drives; RAID arrays; random access memories (RAM); read-only memories (ROM), compact flash (CF) storage devices, secure digital (SD) storage devices, and a memory stick storage devices. Each of hair color device 18, hair health analyzer 22, dispensing and mixing apparatus 24, personal computer 26, and server computer 28 may execute an appropriate operating system, for example, Mac OS, iOS, Android OS, Windows, a custom operating system, or other suitable operating system. (Mac OS is a trademark of Apple Inc. in the United States, other countries, or both; iOS is a trademark of Cisco Systems, Inc.; Android is a trademark of Google Inc. in the United States, other countries, or both; Windows is a trademark of Microsoft Corporation in the United Sates, other countries, or both.)

Figure 2:
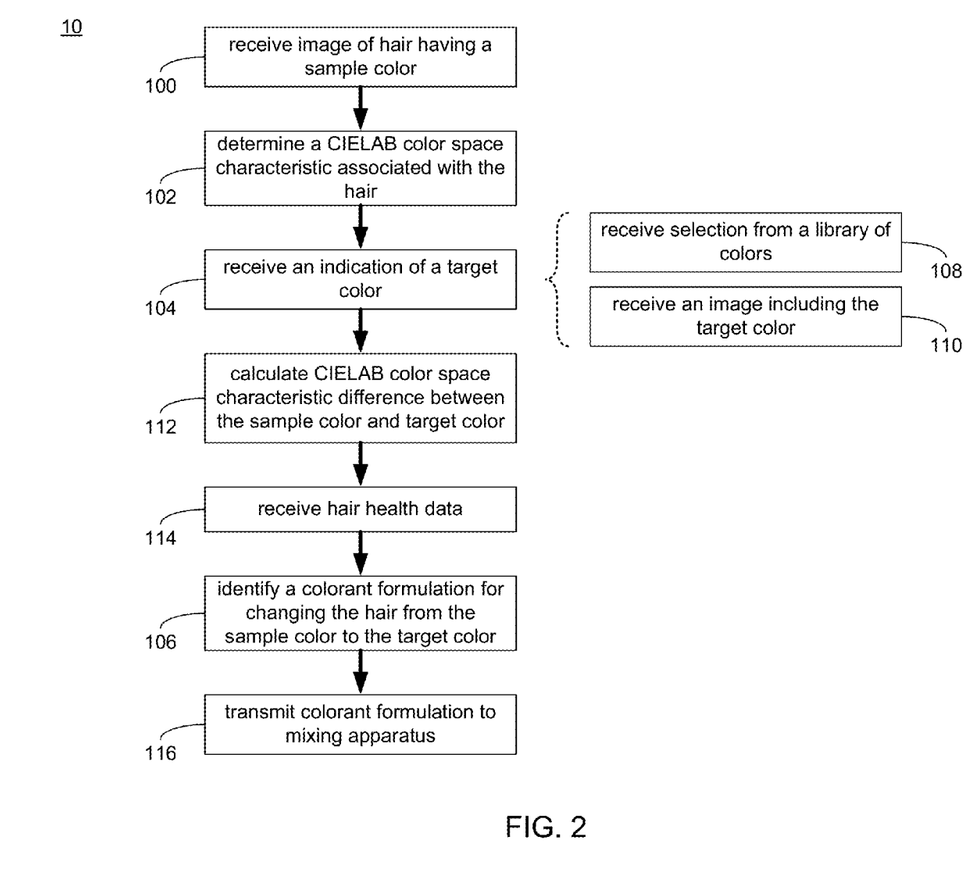
FIG. 2 is a flowchart of the hair coloring process of FIG. 1 according to an embodiment of the present disclosure.

Referring also to FIG. 2, according to an embodiment, hair coloring process 10 may receive 100 an image of hair having a sample color. Hair coloring process 10 may also determine 102 a color space characteristic associated with the hair sample. Hair coloring process 10 may also receive 104 an indication of a target color. Hair coloring process 10 may further identify 106 a colorant formulation for changing the hair from the sample color to a target color.

For example, hair coloring process 10 may receive 100 an image of hair (e.g., of a guest/client of a hair salon desiring a coloring treatment) having a sample color. The sample color may be the current color of the guest's hair, which may be a starting point for a coloring treatment. That is, the sample color may be a color that may be altered to achieve a final color as the result of a coloring treatment. In some embodiments, hair coloring process 10 may receive multiple images of the hair having a sample color. For example, hair coloring process 10 may receive 100 images of the hair corresponding to multiple different locations on the guest's head. As is generally understood, the color of a person's hair may vary for different locations on the person's head. As such, it may be desirable to sample hair from multiple different locations on the guest's head. For example, hair coloring process 10 may receive 100 an image of the hair having a sample color from one or more of the crown, the nape, each side, etc., of the guest's head.

In addition to varying according to different locations on a person's head, the color of a person's hair may vary along the length of the hair, such as the root of the hair, the middle portion of the hair, and the end of the hair. Such variation may be particularly evident in a situation in which the guest has previously received a coloring treatment. As the guest's hair grows, the root portion of the guest's hair may have a color corresponding to a natural hair color for the guest. The middle portion of the hair may have a color corresponding to the previous coloring treatment. Further, the end of the hair may have a color corresponding to the previous coloring treatment, but may further vary based on damage to the hair or the like. As such, in some embodiments, receiving 100 an image of hair including the sample color may include receiving 100 images of the hair from multiple locations on the head and/or multiple locations on the hair.

In an embodiment, hair coloring process 10 may receive 100 an image of the hair having the sample color via hair color device 18. In some embodiments, receiving 100 the image of the hair having the sample color may include capturing an image of the hair, either by the computing device 12 and/or by the hair color device 18.

Figure 3:
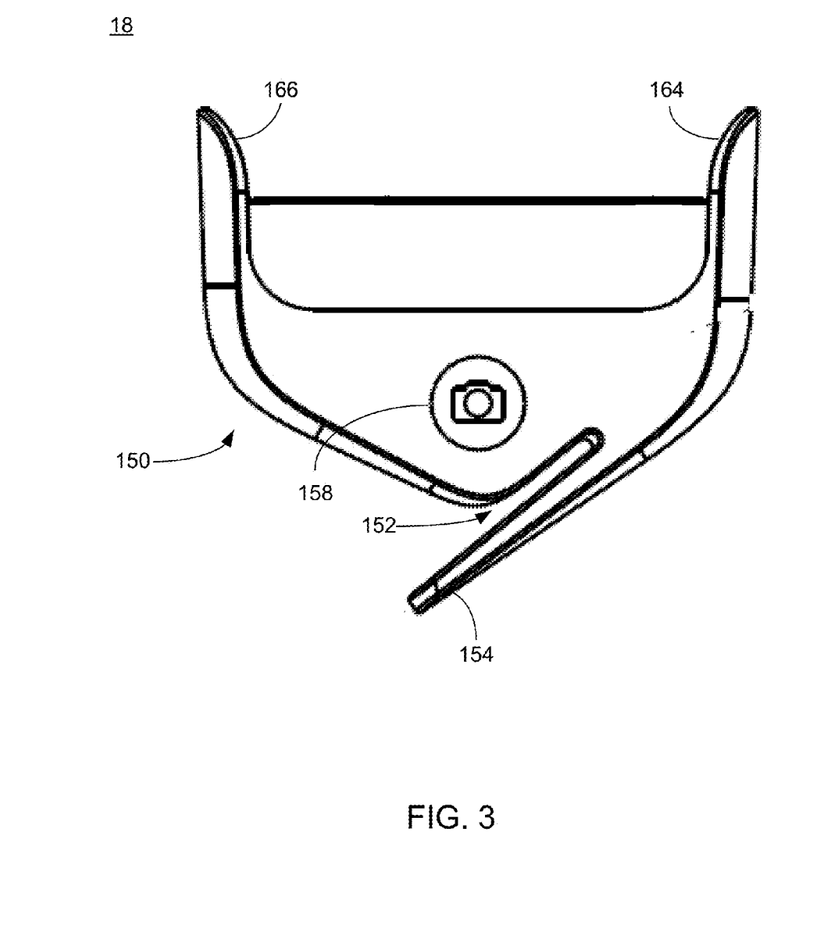
FIG. 3 depicts a hair color measurement device that may be used in connection with the hair coloring process of FIG. 1 according to an embodiment.
Figure 4:
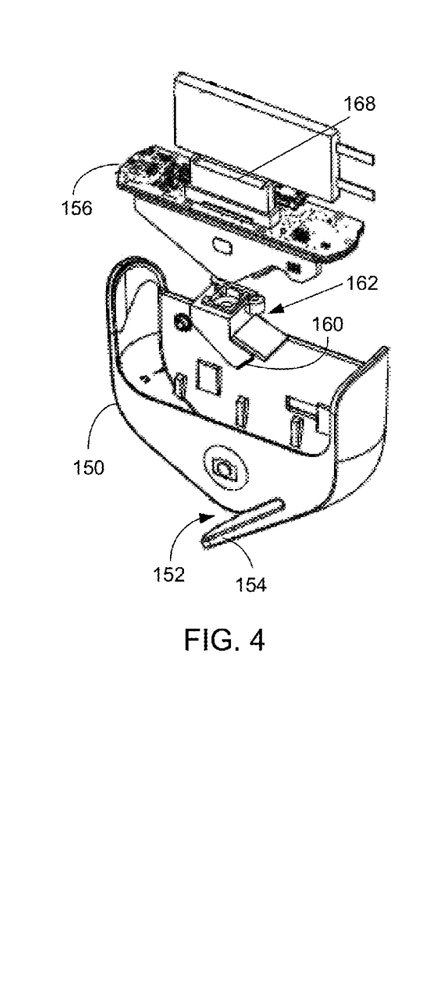
FIG. 4 depicts an exploded view of a portion of the hair color measurement device of FIG. 3 according to an embodiment.

Referring also to FIGS. 3 through 4 an example embodiment of hair color device 18 is shown. In the illustrated embodiment, hair color device 18 may generally include body portion 150 having slot 152 extending through a portion thereof. Body portion 150 may further include guide feature 154 proximate slot 152. Guide feature 154 may be configured to assist a device operator (e.g., user 20, who may be, for example, a colorist at a salon, etc.) in directing the hair into slot 152. In some embodiments, as shown in FIGS. 3 and 4, guide feature 154 may be generally configured as a pick, or comb tine. As such, guide feature 154 may allow user 20 to select a cluster of hair on the guest's head. In an embodiment, guide feature 154 may form a portion of slot 152, allowing user 20 to direct the selected cluster of hair to a proximal region of slot 152.

In an embodiment, hair color device 18 may include an imaging unit (e.g., which may reside on PCB assembly 156 shown in FIG. 4, and/or may otherwise be disposed). The imaging unit may include an image sensor, such as a charge coupled device, CMOS image sensor, or other suitable image sensor. The imaging unit may be configured to output an image acquired by the imaging unit to a computing device (e.g., computing device 12), e.g., via a suitable wired or wireless communication channel between hair color device 18 and computing device 12. Accordingly, in the example embodiment, guide feature 154 may assist user 20 in directing a cluster of the guest's hair into slot 152, and the imaging unit of hair color device 18 may transfer an image of the hair having the sample color to computing device 12.

In an embodiment, computing device 12 may provide a user interface for hair color device 18. For example, an image of the hair received in slot 152 may be displayed on a display screen associated with computing device 12, allowing user 20 to see an image of what is currently located in a focal region of the imaging device. In this manner, the display screen associated with computing device 12 may function as a viewfinder for hair color device 18, allowing user 20 to select an image to be captured. In an embodiment, once a desired image has been composed (e.g., by placement of the guest's hair within slot 152) user 20 may provide a request to capture the image. For example, user 20 may press button 158 associated with hair color device 18 and/or a physical or virtual button provided by computing device 12 to capture an image of the hair disposed within slot 152. In response to receiving the request from user 20 to capture the image, hair coloring process 10 may receive 100 the image of the hair having the sample color.

In an embodiment, the image may include one or more calibration features, e.g., in addition to the image of the hair having the sample color. In some embodiments, the one or more calibration features may include control color patches. The control color patches may include regions of known and/or calibrated colors. Accordingly, the calibration features may allow the sample color of the hair to be determined and/or calibrated based on, at least in part, the known control color patches. As such, any deviation in color imparted to the received 100 image (e.g., by hair color device 18, the imaging unit of hair color device 18, hair coloring process 10, and/or any camera applications or process utilized in connection with determining the sample color) may be accounted for based on, at least in part, the known control color patches.

Figure 5:
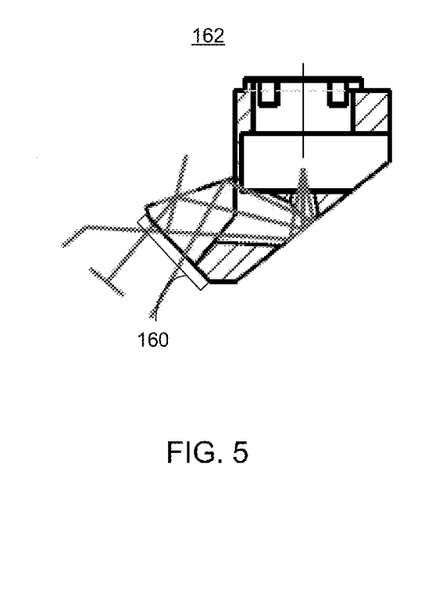
FIG. 5 depicts a prism/mirror unit of the hair color measurement device of FIG. 3 according to an embodiment.

In an embodiment, the calibration features may be included on imaging window 160 disposed at least partially within body portion 150 of hair color device, and adjacent a proximal region of slot 152. In an embodiment, imaging window 160 may be disposed relative to slot 152 such that hair received within slot 152 may be proximate to, and/or at least partially in contact with, imaging window 160. In an embodiment, the calibration feature may be disposed on an imaging plane of imaging window 160. The imaging plane may include a surface of imaging window 160 proximate to and/or at least partially in contact with, the hair. In an embodiment, the imaging unit may include an imaging element arranged to acquire an image in a region adjacent imaging plane of the imaging window. As such, the calibration features may be disposed at the same general focal distance as the hair. Accordingly, the image of the calibration features may be taken through imaging window 160, similar to the image of the hair. As such, any color distortion imparted by imaging window 160 may be generally similarly imparted to the image of the hair and the image of the calibration features. In an embodiment, imaging window 160 may be associated with prism/mirror unit 162. Referring also to FIG. 5, prism/mirror unit 162 may include an optical prism and/or an arrangement of mirrors that may provide a folded optical path between imaging window 160 and the imaging unit of hair color device, thereby increasing the focal distance associated with an image received by the imaging device. Increasing the focal distance associated with the image received by the imaging device may, in some embodiments, "flatten" the image, thereby compressing the perspective of the image, which may, in some embodiments, lessen geometric differences in the subject of the image. Additionally, the use of prism/mirror unit 160 to increase the focal distance may allow for a physically smaller device (e.g., as compared to a device having an equivalent focal length not utilizing a folded optical path).

Figure 6:
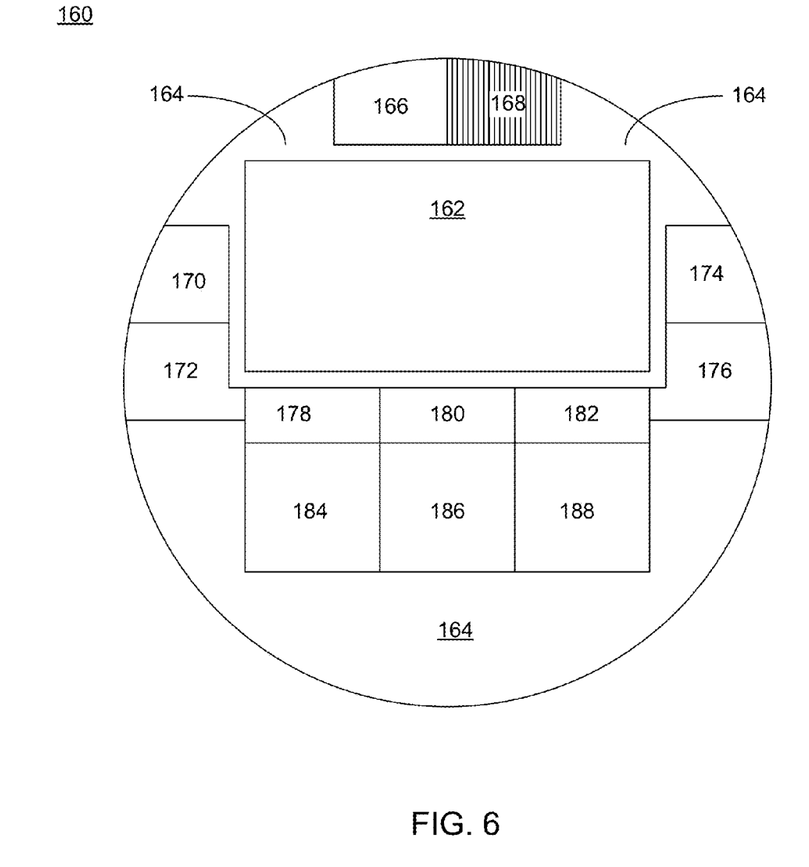
FIG. 6 depicts an imaging window of the hair color measurement device of FIG. 3 according to an embodiment.

Referring also to FIG. 6, an example embodiment of imaging window 160 is shown. In general, imaging window 160 may include open area 162, which may be generally clear. The image of the hair including the sample color may be captured through open area 162. In an embodiment, open area 162 may be generally surrounded by background 164, e.g., which may have a known color (e.g., chroma green). Additionally, in an embodiment, and as described above, imaging window 160 may include one or more calibration features (e.g., calibration features 166-188). Each of calibration features 166-188 may include a known color. For example, in an illustrative embodiment, calibration features 166-188 may include known colors red, dark blue, 18% gray, white, light green, black, yellow, magenta, cyan, dark brown, light brown and light blue, respectively. While general descriptions for the colors associated with each of calibration features 166-188 have been discussed, in an embodiment the respective colors of each of calibration features 166-188 may be quantified to a higher degree of specificity. For example, in an embodiment each of the colors associated with each of respective calibration features 166-188 may be quantified in terms of their respective CIELAB color space characteristics or coordinates (which will be described in greater detail below). As such, in an embodiment, the color of each respective calibration feature 166-188 may be known. Accordingly, an image including one or more of calibration features 166-188 may be color corrected based on the known colors of calibration features 166-188. Accordingly to some embodiments, the white, black and grey calibration features may assist in white balancing and/or color correcting the image. Background 164 and calibration features 166-188 may be applied to imaging window using any suitable printing technique, painting techniques, etching technique, etc.

In addition/as an alternative to including control color patches, the calibration feature may include a feature having a known dimension. For example, as shown, a calibration feature (e.g., calibration feature 168) may include a plurality of stripes having a known dimension (e.g., a known width and/or length). For example, in the illustrated embodiment, the stripes included within calibration feature 168 may include a known width (e.g., 0.02 mm, or other suitable width). In an embodiment, a feature having a known dimension may be used to determine a thickness of hair included in the image, e.g., by reference to the feature having the known dimension. In addition/as an alternative to a calibration feature includes stripes of a known width and/or length, a feature having a known dimension may include a rule printed and/or etched on imaging window 160, a control color patch having one or more known dimensions, and/or another calibration feature having a known dimensions that may be utilized, e.g., to measure and/or estimate a thickness of a hair included in the image and/or a dimension of another feature included within the image.

In an embodiment, hair color device 18 may also include an illumination unit (e.g., which may include one or more LED light sources, and/or other light sources, disposed on PCB assembly 156 shown in FIG. 4, or otherwise disposed). In an embodiment, the illumination unit may be configured to illuminate a region proximate the imaging plane of the imaging window 160. In an embodiment, the illumination unit may provide relatively controlled light conditions for acquiring the image of the hair. Further, the relative arrangement of the imaging unit, the illumination unit and the imaging window may generally provide relatively controlled lighting conditions, image resolution, focal distance for the hair having the sample color and the calibration features.

According to an example embodiment, the body portion 150 of hair color device 18 may be configured to be physically coupled with a mobile computing device (e.g., computing device 12). For example, as shown, body portion 150 may include generally laterally opposed members 164, 166 that may be configured to engage opposed sides of computing device 12. Additionally, body portion may include a recessed region, e.g., which may engage at least a portion of computing device 12. In some embodiments, one or more surfaces of laterally opposed members 164, 166 may include an elastomeric material, e.g., which may increase a frictional engagement of computing device 12. In some embodiments, hair color device 18 may include a communication interface (e.g., connector 168 disposed on PCB assembly 156, and/or otherwise disposed) for communicatively coupling with computing device 12. In some embodiments, connector 168 may provide a pass-through connection, whereby the communication interface between hair color device 18 and computing device 12 may not interfere with communication between computing device 12 and other devices via a corresponding connector. In other embodiments, a wireless communication channel may be established between hair color device 18 and computing device 12. In some embodiments hair color device 18 may include a separate power source (e.g., for powering the imaging unit and/or the illumination unit). In other embodiments, hair color device 18 may be powered by computing device (e.g., via connector 168 and/or another connector). In an embodiment in which hair color device 18 may include a separate power source, the power source may include a rechargeable battery, or other suitable power source.

Interactions between computing device 12 and hair color device 18 (e.g., capturing an image, providing viewfinder functionality, etc.) may be provided by hair coloring process 10, and/or another application or process executed by computing device 12 and/or hair color device 18.

In some embodiments, hair coloring process 10 may be configured to receive 100 the image of the hair having the sample color via camera functionality included within computing device 12. For example, computing device 12, e.g., which may, in some embodiments, include a smartphone that may provide camera functionality, may be utilized to take a picture of the hair using the camera functionality of the computing device. In some embodiments, one or more attachments may be utilized in connection with computing device 12, e.g., for separating a hair sample to be imaged, for providing a desired focal distance, or the like. Such an attachment may, in some embodiments, include one or more lenses and/or illumination features and/or calibration features that may be utilized in conjunction with camera functionality provided by computing device 12.

In an embodiment, hair coloring process 10 may determine 102 a color space characteristic associated with the hair sample, e.g., based on, at least in part, the received 100 image of the hair sample. For illustrative purposes the color space and color space characteristics may generally be described in terms of a CIELAB color space. However, other suitable color spaces may also be utilized. Examples of other suitable color spaces may include, but are not limited to, CIEZYZ color space, Hunter Lab color space, Munsell color system, CIEDE200 color space, and CMC I:c color space. In an illustrative embodiment, a CIELAB color space characteristic associated with the hair sample, e.g., based on, at least in part, the received 100 image of the hair sample. As is generally known CIELAB (also CIE L*a*b*) is a color space specified by the International Commission on Illumination that describes all colors visible to the human eye. The CIELAB color space is a three-dimensional model that utilizes three coordinates to define each color: lightness (designated by L*), green/magenta (designated by a*), and yellow/blue (designated by b*). The CIELAB color space may generally provide a representation of human perception of color, in which changes in a color value in the CIELAB color space may result in a generally equivalent change in human perception of the color.

In an embodiment, hair coloring process 10 may determine 102 a CIELAB color space characteristic associated with the sample color of the hair in the received 100 image, in which the CIELAB color space characteristic may include at least a lightness characteristic of the sample color. In some embodiments, hair coloring process 10 may additionally determine 102 a green/magenta characteristic and/or a yellow/blue characteristic associated with the sample color of the hair in the received 100 image.

Determining 102 the CIELAB color space characteristic may be based on, at least in part, correcting the sample color based on, at least in part, the one or more calibration features included in the image. For example, and as generally discussed above, the calibration feature may include one or more known control colors. Accordingly, a color of the image (including the hair having the sample color) may be adjusted such that the color of the calibration feature included within the image may correspond to the known control color. Various suitable techniques may be utilized for color correcting the image.

Hair coloring process 10 may also receive 104 an indication of a target color. The target color may generally be the desired final color for the hair achieved by a coloring treatment. In an embodiment, receiving 104 the indication of the target color may include received 108 a selection of a color from a library of colors associated with a colorant line (e.g., which may include a professional colorant line). For example, manufacturers of hair colorants may provide libraries of colors that may be achieved using various formulations of hair colorants provided by the manufacturer. The libraries of colors may include printed and/or electronic color swatches and/or software packages in which digital representations of a representative person may be displayed with hair having a color that may be achieved using a colorant formulation provided by the manufacturer. The exact colors provided by different manufacturers may vary from one another. Consistent with an embodiment, a guest and/or colorist at a salon may select a desired target color from a library of colors, e.g., using a printed color chart and/or using an electronic device, such as computing device 12, personal computer 26, and/or another electronic device. In an embodiment, a library of colors may be stored in a database (e.g., database 44, 46 and/or another database associated with one or more computing devices, such as a database residing on one or more of storage device 16 of computing device 12, storage device 36 of hair health analyzer 22, storage device 38 of mixing apparatus 24, or the like) or other electronic repository. One or more of databases 44, 46 may be accessed via computing device 12, and/or personal computer 26.

According to an example embodiment, receiving 104 the indication of the target color may include receiving 110 an image including the target color. For example, a guest may wish to match the target color to the color of an existing item (e.g., an article of clothing, another individual's hair, or any other suitable item). In an embodiment, hair coloring process 10 may receive 110 an image including the target color. Receiving 110 the image including the target color may include receiving an existing electronic image (e.g., which may have been captured by a digital camera, a scanner, or the like) via a suitable communication interface (e.g., an Ethernet interface, a USB interface, accessing an electronic image file stored on a storage device, such as storage device 16, or the like). In an embodiment, the guest may provide the image including the target color, e.g., on a portable storage medium, such as a flash memory drive, via electronic mail, or otherwise provide the image. In some embodiments, hair color device 18 may be utilized to capture an image including the target color in a similar manner as described above for determining the sample color.

In an embodiment, guide feature 154 of hair color device 18 may include a fixed or a removable projection, which may in part define slot 152. In an embodiment in which guide feature 154 may include a removable projection, removal of the projection may at least partially expose imaging window 160. At least partially exposing imaging window 160 may allow the imaging unit to capture images of features that may not be readily amenable to insertion into slot 152. For example, removal of the projection may allow an image of an object or feature including the target color to be captured by hair color device. Further, in some embodiments, the removal of the projection may allow the imaging unit of hair color device 18 to capture an image of the guest's skin, finger nails, or eyes. For example, an image of the guest's skin and/or eyes may be used to determine an amount of melanin that the guest may have in their hair based upon, at least in part, the guest's eye color and skin tone. For example, an image of the guest's iris may be compared to a database of irises or iris colors for determining an estimated amount of melanin that the guest may have naturally in his/her body, and therefore in his/her hair. Similar comparisons of the guest's skin color to a database of skin colors may also be used in connection with determining an estimated amount of melanin for the guest. Adjustments to a colorant formulation may be made based on, at least in part, the determined estimated amount of melanin. Determining estimated melanin amounts may include determining a color space characteristic associated with one or more of the guest's eyes and/or skin in a manner as generally described.

In an embodiment, hair coloring process may calculate 112 a CIELAB color space characteristic difference between the sample color and the target color. Calculating 112 the CIELAB color space characteristic difference between the sample color and the target color may include receiving a CIELAB color space characteristic associated with the target color (e.g., if the CIELAB color space characteristic associated with the target color is known) and/or determining a CIELAB color space characteristic of the target color. In some embodiments, a color space characteristic associated with each of the L*, a*, and b* color space components may be calculated 112. As generally discussed above, a change in a color value in the CIELAB color space may result in a generally equivalent change in human perception of the color.

Hair coloring process 10 may identify 106 a colorant formulation for changing the hair from the sample color to the target color. In an embodiment, identifying 106 the colorant formulation may be based on, at least in part, the CIELAB color space characteristic difference between the sample color and the target color. For example, colorant manufacturers may specify colorant formulations for achieving various color shifts (e.g., changes in lightness and/or changes in hue, undertone, etc.). In an embodiment, identifying 106 the colorant formulation for changing the hair from the sample color to the target color may include accessing formulation data for a particular colorant manufacturer (e.g., whose colorant products may be used in connection with a given coloring treatment). The colorant formulation may include a listing of colorant components and associated quantities that make up the colorant formulation. In an embodiment, identifying 106 the colorant formulation for changing the hair from the sample color to the target color may include accessing a formulation database (e.g., one or more of database 44, 46 and/or another database, as described herein above), for formulation data relative to a desired color shift (e.g., corresponding to the color change for changing the hair from the sample color to the target color).

In an embodiment, hair coloring process 10 may receive 114 hair health data associated with the hair. Further, identifying 106 colorant formulation may include identifying the colorant formulation based on, at least in part, the hair health data. In an embodiment, the hair health data may include one or more characteristics of the sample hair such as, hair thickness data, hair breaking strength data, and hair elasticity data.

Continuing with the above example embodiment, hair colorant formulations may vary depending upon hair health. Further, in some embodiments, a particular color change (e.g., a particular target color in view of a current sample color) may be unadvisable. For example, based on the hair health data, it may be determined whether the hair can be safely colored to achieve the target color. For example, highly processed hair may be stripped of proteins, and may therefore, be severely damaged by the desired color change. In some embodiments, based on the hair health data additional treatments may be recommended, either as pre-coloring treatments or as post coloring treatments, to reduce damage associated with the desired color change. Still further, the hair health data may indicate one or more post-coloring treatments to improve the stability of the color and/or maintain hair health to overcome damage resulting from the coloring process.

In an embodiment, hair coloring process 10 may receive 114 hair health data, at least in part, from hair health analyzer 22. In an embodiment, hair thickness data may be received 114 based on, for example, a comparison of the hair included within the image acquired via hair color device 18 and the one or more calibration features having a known dimension. In an embodiment, hair coloring process 10 may receive 114 one or more of hair breaking strength data and hair elasticity data via hair health analyzer 22. In an embodiment, hair health analyzer 22 may utilize one or more strands of the guest's hair to determine the hair breaking strength data and/or hair elasticity data associated with the guest's hair. In a similar manner to differing hair color associated with different parts of the guest's head, hair health data may similarly differ for different parts of the guest's head. Accordingly, in some embodiments, hair health data may be received 114 associated with hair from different parts of the guest's head.

Figure 7:
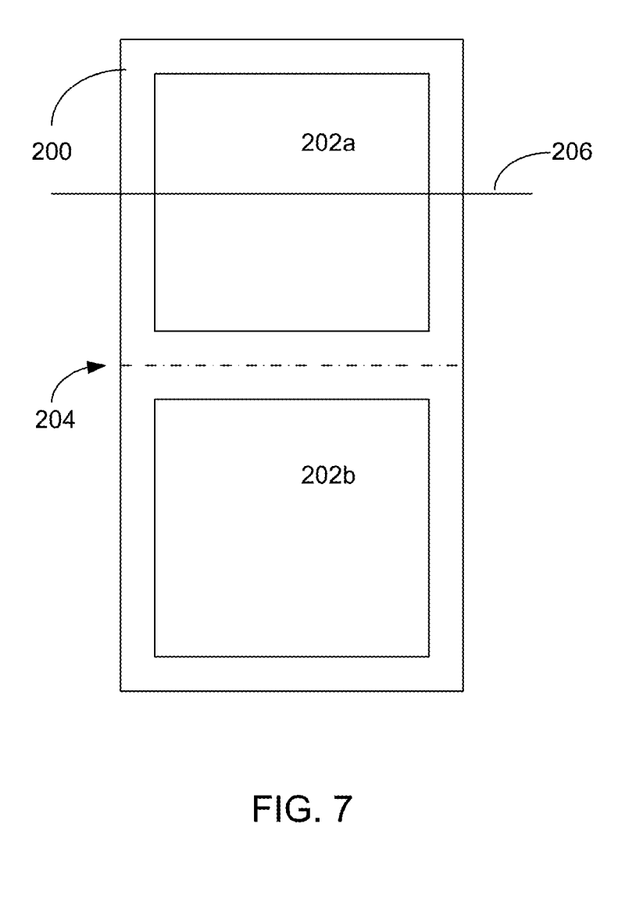
FIG. 7 depicts a testing frame that may be used in connection with the hair health analyzer of FIG. 1 according to an embodiment.
Figure 8:
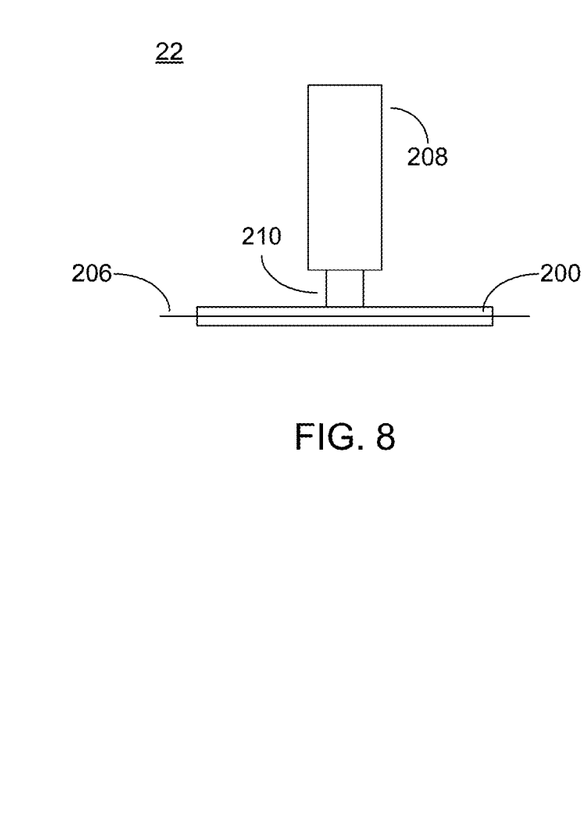
FIG. 8 depicts a hair health analyzer that may be used in connection with the hair coloring process of FIG. 1 according to an embodiment.

Referring also to FIGS. 7 and 8, an example embodiment, of a system that may be utilized for determining hair health data are diagrammatically depicted. In an embodiment, testing frame 200 may be utilized in connection with determining hair health data. Testing frame 200 may be formed of any suitable material, such as paper, cardboard, plastic, metal, etc. In general, testing frame 200 may include two cutouts 202a, 202b. In an embodiment, cutouts 202a, 202b may be generally symmetrical about fold line 204. Fold line 204 may include a crease or line of mechanical weakness extending across frame 200. Fold line 204 may, in some embodiments, facilitate folding frame 200 to generally align cutouts 202a, 202b one over the other. In an embodiment, testing frame 200 may generally resemble a 35 mm slide frame (e.g., cardboard frame utilized for supporting a side). In some embodiments, two separate frames may be utilized, in which each separate frame may include one or more cutouts.

One or more hairs to be tested (e.g., hair 206) may be removed from the guest's head (e.g., by plucking or cutting). As generally discussed above, in some embodiments, hair from different regions of the guest's head may be tested to determine any variations in hair health. Hair 206 may be generally placed across frame 200 in the region of one cutout (e.g., cutout 202a). According to various embodiments, hair 206 may be stretched taught across cutout 202a. In an embodiment, at least a portion of frame 200 may include a pressure sensitive adhesive, e.g., to facilitate maintaining the position of hair 206 once placed across cutout 202a. With hair 206 place across cutout 202a, frame 200 may be folded about fold line 204 to orient cutouts 202a, 202b one over the other. In such a configuration, hair 206 may be disposed between the two halves of frame 200 delineated by fold line 204. In an embodiment in which frame 200 may include a pressure sensitive adhesive, the pressure sensitive adhesive may maintain the frame 200 in the folded configuration.

Referring also to FIG. 8, hair health analyzer 22 may include test actuator 208 and test arm 210. In general, with hair 206 loaded in test frame 200 in the above-described manner, test frame 200 may be maintained in position relative to test actuator 208 and test arm 210 (e.g., using any suitable support structures, not shown). Test actuator 208 may be activated to move test arm 210 relative to test frame 200 such that test arm may engage hair 206. Test arm 210 may be moved relative to test frame 200 in a direction generally normal to hair 206 until hair 206 breaks under the force provided by test arm and test actuator. Other testing configurations may similarly be utilized for determining hair health data of the hair, including, but not limited to, a configuration that may apply a force parallel to the length of the hair.

In an embodiment, test actuator 208 may include a linear actuator, a stepper motor, or other actuator whose movement may be relatively precisely controlled. The movement of test actuator 208 (and/or test arm 210 coupled thereto) may be monitored by an encoder (e.g., an optical, mechanical, magnetic, or other suitable encoder). In such an embodiment, the movement of test actuator 210 (and/or test arm coupled thereto) may be monitored and/or controlled (e.g., via a feedback controller). Consistent with the foregoing description the force applied to hair 206 may be relatively precisely controlled (e.g., based on an applied voltage, etc., depending upon the nature of the test actuator). Accordingly, the breaking strength of hair 206 may be determined based on the force applied to hair 206 by test actuator 208 and may be measured by a strain gauge or other force sensing device. Similarly, the travel distance of test actuator 208 (and/or test arm 210) may be determined based on the applied control of the test actuator (e.g., duration of movement, number of steps moved, etc.) and/or via an output from an encoder. Accordingly, in an embodiment an elasticity of hair 206 may be determined, e.g., based on, at least in part, the travel distance of test actuator 208 (and/or test arm 210) from the point at which hair 206 was engaged by test arm 210 until breakage of hair 206. The hair health data determined by hair health analyzer 22 may be received 114 by hair coloring process 10 (e.g., from hair health analyzer 22). Various additional/alternative configurations may similarly be utilized to determine hair health data.

In an embodiment, hair coloring process 10 may receive 114 hair health data associated with the hair, and may identify 106 a colorant formulation may based on, at least in part, the hair health data. The hair colorant formulation identified 106 based on, at least in part, the hair health data associated with the hair may include, for example, a recommendation not to color the hair to the target color, a recommendation of one or more pre-coloring treatments for the hair, and/or a recommendation of one or more post-coloring treatments for the hair. The colorant formulation may be otherwise based on, at least in part, the hair health data.

In an embodiment, hair coloring process 10 may further transmit 116 the identified 106 colorant formulation to a dispensing and mixing apparatus (e.g., apparatus 24). In general, dispensing and mixing apparatus 24 may assist in measuring and combining the components of the colorant formulation in correct amounts. For example, dispensing and mixing apparatus 24 may provide automated and/or semi-automated dispensing and mixing of the components of the colorant formulation, and/or may provide instructions, prompts and/or feedback to assist a user (e.g., user 20) in dispensing and mixing the components of the colorant formulation. Accordingly, in some embodiments dispensing and mixing apparatus 24 may facilitate accurately achieving the desired colorant formulation, while reducing user error, such as variability that may occur from mixing the components by eye, or other relatively imprecise measurement technique. Dispensing and mixing apparatus 24 may, therefore, in some embodiments reduce waste and increase efficiency and/or repeatability of the preparation of a colorant formulation.

Figure 9:
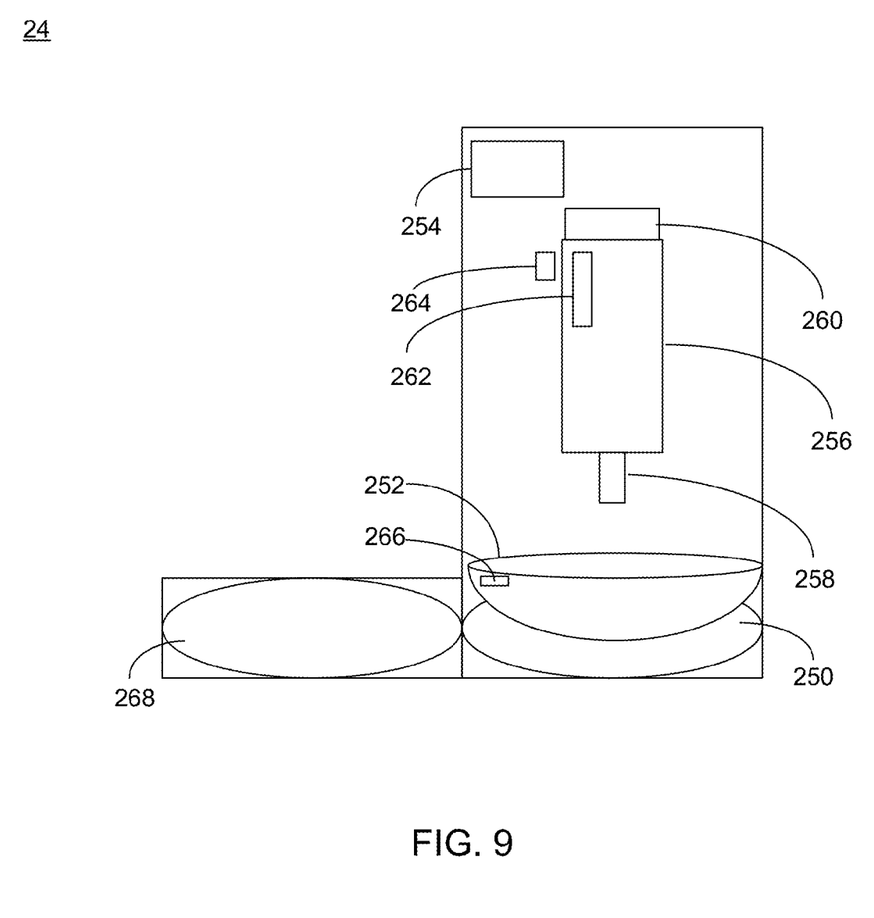
FIG. 9 depicts a dispensing and mixing apparatus that may be used in connection with the hair coloring process of FIG. 1 according to an embodiment.

Referring also to FIG. 9, an example embodiment of dispensing and mixing apparatus 24 is depicted. In an embodiment, dispensing and mixing apparatus 24 may receive the colorant formulation transmitted 116 by hair coloring process 10 (e.g., via computing device 12). The transmitted 116 hair colorant formulation may include an indication of the components of the hair colorant formulation and an indication of a respective quantity or proportion of each of the components. In some embodiments, the transmitted 116 colorant formulation may include an indication of the color change required to achieve the target color. According to such an embodiment, dispensing and mixing apparatus 24 may receive (e.g., in response to a request by dispensing and mixing apparatus 24 and/or another device) colorant formulation information including component information and proportion information, e.g., from a database (e.g., such as database 44, 46 and/or another database).

In an embodiment, dispensing and mixing apparatus 24 may include scale 250 that may be configured to weigh a mixing container (e.g., bowl 252) that may be placed on scale 250. Scale 250 may, in this arrangement, weigh bowl 252 and/or any colorant components (or other contents) added to scale 250. In an embodiment, dispensing and mixing apparatus 24 may include user interface 254. User interface 254 may include, for example, a display screen and/or one or more user interface controls such as buttons (e.g., physical buttons and/or virtual buttons provided via a touch-screen interface). In various embodiments, user interface 254 may display an indication of a colorant component to be added to bowl 252 (e.g., for the purpose of achieving the colorant formulation for the guest). In some embodiments, user interface 254 may display a weight of the component to be added (e.g., which may be decremented and/or incremented in response to the addition of the component to bowl 252), a weight measured by scale 250, and/or a tare weight. In an example embodiment, once a prescribed quantity of a colorant component has been added to bowl 252 (e.g., based on the transmitted 116 colorant formulation), user interface 254 may provide an indicator (e.g., a visual and/or audible indicator) that the prescribed quantity of the colorant component has been added to bowl 252. In an embodiment, once a prescribed quantity of a first colorant component has been added to bowl 252, user interface 254 may provide an indication of a second colorant component to be added to bowl 252 and/or a quantity of the second colorant to be added to bowl 252, based on the colorant formulation.

In an embodiment, a user (e.g., user 20) may manually dispense colorant components into bowl 252 to achieve the colorant formulation. User interface 254 may provide instructions, prompts, quantity of component to add, quantity of component added, total weight of the formulation being prepared, etc., to aid user 20 in preparing the colorant formulation. In some embodiments, mixing apparatus 24 may provide automated and/or semi-automated dispensing of colorant components. In such an embodiment, mixing apparatus 24 may be configured to dispense a required amount of one or more colorant components (e.g., into bowl 252). In an embodiment, mixing apparatus 24 may include control system (e.g., a set-point controller, a proportional-integral-derivative controller, or other suitable control system) that may operate in conjunction with scale 250 for providing controlled dispensing of the one or more colorant components, e.g., based on a measured weight of dispensed colorant component.

With reference still to FIG. 9, in an embodiment colorant components may include syringe-type cartridge (e.g., cartridge 256), which may generally include a generally hollow body including a plunger slidably disposed at least partially within the hollow body. Movement of the plunger within the generally hollow body may dispense colorant component contained within the generally hollow body via cartridge nozzle 258. In an embodiment, each colorant component cartridge (e.g., cartridge 256) may include a nozzle (e.g., nozzle 258), which may reduce and or eliminate the occurrence of cross contamination resulting from dispensing multiple different colorant components through the same nozzle.

Consistent with the illustrated embodiment, user 20 may couple cartridge 256 with mixing apparatus 24 such that dispensing mechanism 260 may engage the plunger of cartridge 256. Dispensing mechanism 260 may include one or more actuators (e.g., linear actuators, motors, servos, stepper motors, etc.) and/or associated linkages, drive trains, or the like, configured to exert a force on the plunger of cartridge 256 for dispensing the colorant component from cartridge 256 into bowl 252. As generally discussed above, mixing apparatus 24 may include a control system for controlling dispensing mechanism 260 (e.g., based on a dispensed weight measured by scale 250, a measured travel of dispensing mechanism 260 and/or the plunger of cartridge 256, etc.) for dispensing a controlled amount of the colorant component, e.g., based on the colorant formulation.

In addition/as an alternative to syringe-type cartridge 256, various colorant component containers may be utilized in connection with a mixing apparatus. For example, and as in commonly known, in an embodiment the containers for the colorant components may include squeeze tubes that may be squeezed or crushed to dispense the colorant component via a nozzle or opening of the squeeze tube. In such an embodiment, the dispensing mechanism may include a pair of pinch rollers, for example, that may pinch and squeeze the tube to dispense the colorant component from the tube. In a similar manner, the dispensing mechanism may include a turn-key, which may include a spindle having a longitudinal slot or opening. A portion of the squeeze tube (e.g., a distal end of the squeeze tube relative to the nozzle) may be at least partially received in the longitudinal slot or opening. The turn-key may be rotated relative to the squeeze tube to dispense the colorant component from the squeeze tube. Various additional/alternative containers and corresponding dispensing mechanisms may be utilized in connection with the mixing apparatus.

In an embodiment, dispensing and mixing apparatus 24 and/or hair coloring process 10, may provide user 20 instructions and/or prompts for preparing the colorant formulation, e.g., via user interface 254, computing device 12, or another device. The instructions and/or prompts for preparing the colorant formulation may include an indication of each colorant component to be included in the colorant formulation, and may include an indication of the quantity of each colorant component to be included in the colorant formulation. In an embodiment, the instructions and/or prompt may sequentially identify the colorant components to be included in the colorant. For example, dispensing and mixing apparatus 24 and/or hair coloring process 10 may provide (e.g., via user interface 254) an indication of a first colorant component to be included in the colorant formulation. Once the appropriate quantity of the colorant component has been added (e.g., based on a weight measured by scale 250, and/or a measurement otherwise provided by mixing apparatus 24, such as based on a travel of a dispensing mechanism actuator, or the like), dispensing and mixing apparatus and/or hair coloring process 10 may provide an indication of a second colorant component to be included in the colorant formulation. Indications of additional colorant components may be provided, e.g., in response to determining that an appropriate quantity of the preceding colorant component has been added. In an example embodiment, user 20 may provide an indication that an appropriate amount of a colorant component has been added to the colorant formulation, such as by selecting a next button via user interface 254, computing device 12, or another device. As described above, the one or more colorant components may be dispensed manually by user 20 and/or in an automated/semi-automated manner by dispensing and mixing apparatus 24.

In an embodiment, one or more of the colorant component cartridges may include an identifier (e.g., identifier 262) that may be interrogated (e.g., by interrogation system 264) by dispensing and mixing apparatus 24 (or another device), e.g., to verify that the appropriate colorant component is being used. Examples of identifiers may include, but are not limited to, barcodes (e.g., which may include system specific barcodes, SKU codes, ultraviolet barcodes, and the like), RFID transponders, or other suitable identifier. In an embodiment, dispensing and mixing apparatus 24 may interrogate the identifier associated with the colorant component cartridge when the cartridge is coupled to dispensing and mixing apparatus 24 for dispensing the colorant component from the cartridge. As such, dispensing and mixing apparatus 24 may verify that the appropriate colorant component has been installed prior to dispensing the colorant component. In other embodiments, the identifier associated with the colorant component cartridge may be interrogated prior to being coupled with dispensing and mixing apparatus 24 (e.g., for either manual dispensing of the colorant component and/or for automated/semi-automated dispensing of the colorant component). In some embodiments, verifying that the appropriate colorant component is being utilized may reduce and/or eliminate errors in the preparation of the colorant formulation. Any suitable interrogation system (e.g., optical barcode reader, RFID interrogation system, etc.) may be utilized as appropriate to the identifier.

In a similar manner, bowl 252 may include identifier 266 that may be interrogated by dispensing and mixing apparatus 24 (e.g., by interrogation system 264) and/or by another device. Identifier 266 associated with bowl 252 may include any suitable identifier (e.g., RFID transponder, barcode, etc.). In an embodiment, hair coloring process 10 may associate identifier 266 with the hair colorant formulation and/or with the guest for whom the hair colorant formulation is being prepared. In some embodiment, the hair colorant formulation prepared by dispensing and mixing apparatus 24 may vary from the colorant formulation transmitted 116 to mixing apparatus 24. For example, a sufficient quantity of one or more of the colorant components may not be available, an incorrect quantity of one or more of the colorant components may be utilized, etc. According to an embodiment, hair coloring process 10 and/or dispensing and mixing apparatus 24 may store (e.g., on one or more of storage devices 16, 38) the as-mixed formulation, e.g., which may include an indication of the colorant components and respective quantities of the colorant components included in the colorant formulation that was actually prepared.

In an embodiment, hair coloring process 10 may store the colorant formulation as part of a guest record (e.g., for future reference, etc.) Further, while not shown, an identifier 266 associated with bowl 252 may be interrogated prior to applying the colorant formulation to the guest, e.g., to verify that the proper hair colorant formulation is being applied to the proper guest.

In an embodiment, dispensing and mixing apparatus 24 may include a mixer (e.g., mixer 268). Mixer 268 may include, for example, a magnetic stirrer, a mechanical mixer, or the like. Mixer 268 may facilitate suitable mixing of the colorant components during the preparation of the colorant formulation. According to various embodiments, mixer 268 may stir the colorant components for a predetermined period of time and/or a period of time indicated by user 20 (e.g., in response to user 20 starting and stopping mixer 268, setting a timer, etc.). In some embodiments, mixer 268 may stir the colorant component until a desired viscosity of the colorant formulation is achieved. While mixer 268 is shown as a separate component from scale 250, in the illustrated embodiment, it will be appreciated that in some embodiments the mixer may be integrated into the scale.

In an embodiment, after the coloring treatment has been completed, the bowl may be reweighed, e.g., to determine the amount of colorant formulation used during the coloring treatment. For example, in an embodiment in which the colorant formulation may be associated with a bowl (e.g., based on, at least in part, identifier 266), a weight of the colorant formulation as-prepared may be stored in the guest record, and/or otherwise stored. Hair coloring process 10 may determine the amount of colorant formulation used during the coloring treatment based on the difference between the as-prepared weight of the colorant formulation and the reweighed weight of the bowl. In an embodiment, the amount of the colorant formulation used for the coloring treatment may be utilized to prevent future waste, e.g., during subsequent coloring treatments for the guest.

In an embodiment, once the coloring treatment is complete, the guest's hair may be re-sampled to determine the color of the hair after the coloring treatment. In an embodiment, hair color device 18 may be utilized to capture an image of the guest's hair after the coloring treatment. Hair coloring process 10 may determine the color of the guest's hair after the coloring treatment in a generally similar manner as determining the sample color of the guest's hair (e.g., prior to the coloring treatment). In some embodiments, hair coloring process 10 may determine a difference between the target color and the color of the guest's hair after the coloring treatment. Any determined differences between the color of the guest's hair after the coloring treatment and the target color may be utilized, for example, to adjust further coloring formulations for the guest and/or for other guests.

Figure 10:
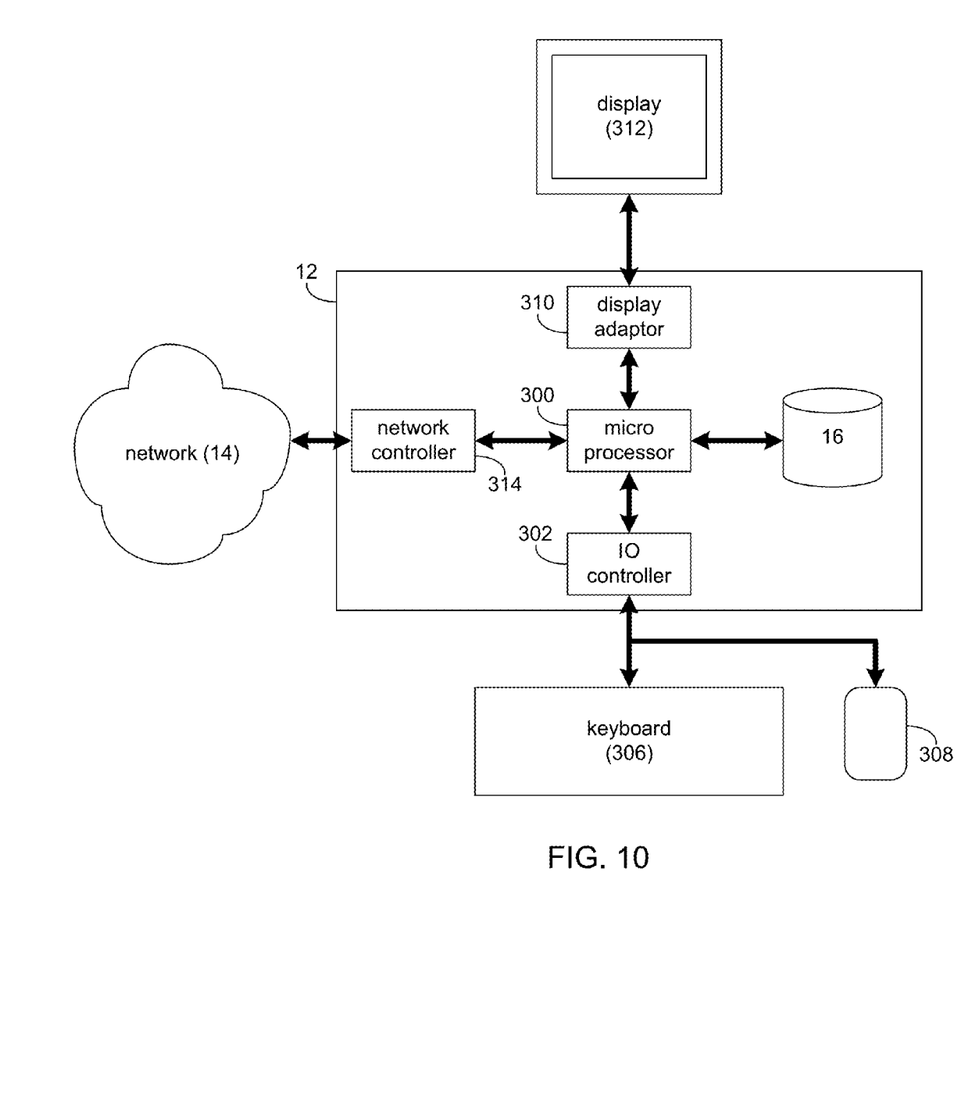
FIG. 10 is a diagrammatic view of the computing device of FIG. 1 according to an embodiment of the present disclosure.

Referring also to FIG. 10, there is shown a diagrammatic view of computing device 12. While computing device 12 is shown in this figure, this is for illustrative purposes only and is not intended to be a limitation of this disclosure, as other configuration are possible. For example, any computing device capable of executing, in whole or in part, hair coloring process 10 may be substituted for computing device 12 within FIG. 10, examples of which may include but are not limited to hair color device 18, hair health analyzer 22, mixing apparatus 24, personal computer 26, and server computer 28.

Computing device 12 may include microprocessor 300 configured to e.g., process data and execute instructions/code for hair coloring process 10. Microprocessor 300 may be coupled to storage device 16. As discussed above, examples of storage device 16 may include but are not limited to: a hard disk drive; a tape drive; an optical drive; a RAID device; an NAS device, a Storage Area Network, a random access memory (RAM); a read-only memory (ROM); and all forms of flash memory storage devices. IO controller 302 may be configured to couple microprocessor 300 with various devices, such as keyboard 306, mouse 308, USB ports (not shown), and printer ports (not shown). Display adaptor 310 may be configured to couple display 312 (e.g., a CRT or LCD monitor) with microprocessor 300, while network adapter 314 (e.g., an Ethernet adapter) may be configured to couple microprocessor 300 to network 14 (e.g., the Internet or a local area network).

As will be appreciated by one skilled in the art, the present disclosure may be embodied as a method (e.g., executing in whole or in part on computing device 12), a system (e.g., computing device 12), or a computer program product (e.g., encoded within storage device 16). Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium (e.g., storage device 16) having computer-usable program code embodied in the medium.

Any suitable computer usable or computer readable medium (e.g., storage device 16) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor (e.g., processor 300) of a general purpose computer/special purpose computer/other programmable data processing apparatus (e.g., computing device 12), such that the instructions, which execute via the processor (e.g., processor 300) of the computer or other programmable data processing apparatus, create means for implementing the functions/acts specified in the flowchart and/or block diagram block or blocks.

These computer program instructions may also be stored in a computer-readable memory (e.g., storage device 16) that may direct a computer (e.g., computing device 12) or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer (e.g., computing device 12) or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

Having thus described the disclosure of the present application in detail and by reference to embodiments thereof, it will be apparent that modifications and variations are possible without departing from the scope of the disclosure defined in the appended claims.

What is claimed is:

1. An apparatus comprising:
   a body portion having a slot extending through a portion thereof and a guide feature proximate the slot, the guide feature configured to assist directing hair into the slot, the guide feature including one of a fixed projection and a removable projection;
   an imaging window disposed at least partially within the body portion adjacent a proximal region of the slot, the imaging window including a calibration feature disposed on an imaging plane of the imaging window, the imaging plane of the imaging window and the calibration feature having a common focal distance, the imaging window including an open area through which an image of the hair can be captured;
   an illumination unit configured to illuminate a region proximate the imaging plane of the imaging window; and
   an imaging unit including an imaging element arranged to acquire an image in a region adjacent imaging plane of the imaging window.

2. The apparatus according to clam 1, wherein the calibration feature includes one or more color patches.

3. The apparatus according to claim 1, wherein the calibration feature includes a feature having a known dimension.

4. The apparatus according to claim 1, wherein the body portion is configured to be coupled with a mobile computing device.

5. The apparatus according to claim 1, wherein the imaging unit includes one or more processors configured to output an image acquired by the imaging unit to a computing device.

* * * * *